(12) United States Patent
Dirksen et al.

(10) Patent No.: US 11,386,883 B2
(45) Date of Patent: Jul. 12, 2022

(54) ACOUSTIC LENS FOR AN ULTRASOUND ARRAY

(71) Applicant: KONINKLIJKE PHILIPS N.V., Eindhoven (NL)

(72) Inventors: Peter Dirksen, Eindhoven (NL); Sergei Shulepov, Eindhoven (NL); Franciscus Johannes Gerardus Hakkens, Eindhoven (NL); Petrus Henricus Maria Timmermans, Eindhoven (NL); Lucas Johannes Anna Maria Beckers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 636 days.

(21) Appl. No.: 16/062,656

(22) PCT Filed: Dec. 16, 2016

(86) PCT No.: PCT/EP2016/081526
§ 371 (c)(1),
(2) Date: Jun. 15, 2018

(87) PCT Pub. No.: WO2017/103172
PCT Pub. Date: Jun. 22, 2017

(65) Prior Publication Data
US 2018/0374471 A1    Dec. 27, 2018

(30) Foreign Application Priority Data
Dec. 18, 2015  (EP) .................................. 15200991

(51) Int. Cl.
*G01K 11/30*    (2006.01)
*G10K 11/30*    (2006.01)
(Continued)

(52) U.S. Cl.
CPC ............ *G10K 11/30* (2013.01); *A61B 8/4444* (2013.01); *A61B 8/4494* (2013.01);
(Continued)

(58) Field of Classification Search
CPC ..... G10K 11/30; A61B 8/4444; A61B 8/4494; B06B 1/0292; G01N 29/221; G01N 29/2406
See application file for complete search history.

(56) References Cited

U.S. PATENT DOCUMENTS 4,387,720 A * 6/1983 Miller .................... G10K 11/30
                                                    600/472
4,503,861 A * 3/1985 Entrekin .................. A61B 8/02
                                                    310/335
(Continued)

FOREIGN PATENT DOCUMENTS

CN    102170938 A    8/2011
CN    104889042 A    9/2015
(Continued)

OTHER PUBLICATIONS

Fujii, Jan. 1995, Japanese Journal of Applied Physics, vol. 34, pp. 312-315, Acoustic Properties of Lens Material for Ultrasonic Probes (Year: 1995).*

(Continued)

*Primary Examiner* — James R Hulka
*Assistant Examiner* — Vikas Atmakuri

(57) ABSTRACT

An acoustic lens suitable for a CMUT array (74) is provided. The acoustic lens comprising: a first layer (47) comprising a thermoset elastomer having a polymeric material selected from hydrocarbons, wherein the first layer has an inner surface (72) arranged to face the array and an outer convex shaped surface (40) arranged to oppose the inner surface; and a second layer (42) coupled to the outer surface of the
(Continued)

first layer and comprising thermoplastic polymer polymethylpentene and an elastomer selected from the polyolefin family (POE) blended therein, wherein the outer layer located at the outer surface of the acoustic window layer, wherein the first layer has a first acoustic wave velocity (v1) and the second layer has a second acoustic wave velocity (v2), said second velocity is larger than the first acoustic wave velocity.

10 Claims, 6 Drawing Sheets

(51) Int. Cl.
    *B06B 1/02*      (2006.01)
    *A61B 8/00*      (2006.01)
    *G01N 29/22*      (2006.01)
    *G01N 29/24*      (2006.01)

(52) U.S. Cl.
    CPC ......... *B06B 1/0292* (2013.01); *G01N 29/221* (2013.01); *G01N 29/2406* (2013.01)

(56) References Cited

U.S. PATENT DOCUMENTS

| | | | | |
|---|---|---|---|---|
| 4,699,150 A * | 10/1987 | Kawabuchi | ............ | G10K 11/30 600/446 |
| 4,880,012 A * | 11/1989 | Sato | ............ | A61B 8/4281 600/472 |
| 5,050,128 A * | 9/1991 | Saitoh | ............ | G10K 11/02 367/7 |
| 5,423,220 A * | 6/1995 | Finsterwald | ............ | B06B 1/0622 310/322 |
| 5,577,507 A * | 11/1996 | Snyder | ............ | A61B 8/4281 600/472 |
| 5,984,871 A * | 11/1999 | TenHoff | ............ | G10K 11/30 310/335 |
| 7,750,536 B2 * | 7/2010 | Chaggares | ............ | H01L 41/083 310/334 |
| 7,888,847 B2 * | 2/2011 | Dietz | ............ | G10K 11/30 310/334 |
| 8,292,818 B2 * | 10/2012 | Yamashita | ............ | A61B 8/4281 600/472 |
| 8,316,518 B2 * | 11/2012 | Lukacs | ............ | A61B 8/543 29/25.35 |
| 8,801,615 B2 * | 8/2014 | Fernandez | ............ | A61N 7/022 600/439 |
| 8,847,467 B2 * | 9/2014 | Chaggares | ............ | H01L 41/083 310/334 |
| 2005/0261590 A1 * | 11/2005 | Ogawa | ............ | G10K 11/26 600/459 |
| 2008/0284287 A1 * | 11/2008 | Yoshimura | ............ | B06B 1/0292 310/365 |
| 2009/0086331 A1 * | 4/2009 | Gunasekaran | ............ | G02B 1/06 359/666 |
| 2011/0062824 A1 * | 3/2011 | Wada | ............ | B06B 1/0629 310/334 |
| 2011/0319768 A1 * | 12/2011 | Saito | ............ | A61B 8/4281 600/472 |
| 2013/0301394 A1 * | 11/2013 | Chen | ............ | B06B 1/0292 367/155 |
| 2014/0265728 A1 * | 9/2014 | Li | ............ | G01N 29/06 310/321 |
| 2014/0345385 A1 * | 11/2014 | Irisawa | ............ | A61B 8/4416 73/609 |
| 2015/0173625 A1 * | 6/2015 | Chaggares | ............ | A61B 5/0095 600/407 |
| 2015/0257734 A1 * | 9/2015 | Chaggares | ............ | H01L 41/253 600/447 |
| 2016/0203809 A1 * | 7/2016 | Brock-Fisher | ............ | G10K 11/002 600/459 |
| 2018/0065148 A1 * | 3/2018 | Beckers | ............ | B06B 1/0292 |

FOREIGN PATENT DOCUMENTS

| | | | |
|---|---|---|---|
| CN | 107405648 A | | 11/2017 |
| JP | 5672823 B2 * | | 2/2015 |
| WO | 2009112025 A2 | | 9/2009 |
| WO | 2017081138 A1 | | 5/2017 |

OTHER PUBLICATIONS

Fujii, Acoustic Properties of Lens Materials for Ultrasonic Probes, 1994, Jpn. J. Appl. Phys, vol. 34, pp. 312-315 (Year: 1994).*

* cited by examiner

ACOUSTIC LENS FOR AN ULTRASOUND ARRAY

This application is the U.S. National Phase application under 35 U.S.C. § 371 of International Application No. PCT/EP2016/081526, filed on Dec. 16, 2016, which claims the benefit of EP Application Serial No. 15200991.6, filed Dec. 18, 2015. These applications are hereby incorporated by reference herein.

FIELD OF THE INVENTION

The invention relates to an acoustic lens for an ultrasound array of capacitive micromachined transducers. The invention further relates an ultrasound probe comprising such an acoustic lens.

BACKGROUND OF THE INVENTION

Recent progress in semiconductor technology resulted in the development of capacitive micro-machined ultrasound transducers (CMUT). These transducers are considered to be potential candidates to replace the conventional piezoelectric based ultrasound transducers (PZT). A CMUT transducer cell comprises a cavity with a movable mechanical part also called a membrane and a pair of electrodes separated by the cavity. When receiving ultrasound waves, ultrasound waves cause the membrane to move or vibrate and change the capacitance between the electrodes which can be detected. Thereby the ultrasound waves are transformed into a corresponding electrical signal. Conversely, an electrical signal applied to the electrodes causes the membrane to move or vibrate, thereby transmitting ultrasound waves.

Advantages of CMUTs are that they can be made using semiconductor fabrication processes and, therefore, may be easier integrated with application-specific integrated circuitry (ASIC); CMUT transducers offer low cost, extended frequency range and finer acoustic pitch over traditional PZTs. Inherently from the PZT based technology most of the commonly used ultrasound arrays with CMUTs have acoustic windows or lens materials selected from the materials used for the PZT-based transducers, such as silicon rubbers, for example RTV.

U.S. Pat. No. 4,880,012 discloses a composite acoustic lens suitable for application with a piezoelectric (PZT) based array. The acoustic lens of U.S. Pat. No. 4,880,012 comprises a first layer bonded to the upper surface of the acoustic matching layer being in contact with the PZT array and a second acoustic lens layer bonded to the upper bonded to the upper surface of the first layer. This acoustic lens converges ultrasound waves generated by the array by providing the second acoustic lens layer having a higher attenuation than the first layer such that at the interface the wave has the constant losses at any coordinate. The first layer of the acoustic lens of U.S. Pat. No. 4,880,012 is made of a silicon rubber containing no filler and showing the sound velocity of about 1000 m/s. The second acoustic lens layer is made of a silicone rubber containing a filler such as aluminum oxide to increase its ultrasound attenuation coefficient.

However, the CMUT possesses different to the PZT mechanism of an electro-acoustical transformation, wherein an interactions between the CMUT membranes and the acoustic materials used for lens may reduce the acoustic performance of the transducer. It was discovered that traditional filled silicon rubbers (also referred here as room temperature curing rubber or RTV) acoustic lens materials, which are easily cast in place and formed by molding into a desired shape, brought in contact with the CMUT array introduce an additional acoustic losses in the CMUT array in addition to normal frequency dependent attenuation. This loss is manifested in increased attenuation on the order of 2 dB and a downshift in center frequency of up to 4 MHz.

There is a need in providing an improved acoustic lens suitable for the CMUT-based ultrasound array for acoustic wave transmission, wherein the CMUT cells are adapted to operate in both: conventional and collapsed operation modes.

SUMMARY OF THE INVENTION

It is an object of the present invention to provide an acoustic lens for an ultrasound array comprising capacitive micromachined transducers, which provides improved acoustic wave propagation combined with chemical and mechanical stability of the layer.

This object is achieved according to the invention by providing an acoustic lens comprising: a first layer comprising a thermoset elastomer having a polymeric material selected from a hydrocarbon family, wherein the first layer has an inner surface arranged to face the array and an outer convex shaped surface arranged to oppose the inner surface; and a second layer coupled to the outer surface of the first layer and comprising thermoplastic polymer polymethylpentene and an elastomer selected from the polyolefin family (POE) blended therein for acoustic impedance adjustment of the second layer, wherein the first layer has a first acoustic wave velocity (v1) and the second layer has a second acoustic wave velocity (v2), said second velocity is larger than the first acoustic wave velocity.

The acoustic lens of the present invention advantageously combines a use of two materials suitable for providing an acoustic wave converging lens applicable with the CMUT array. The first layer of the thermoset elastomer has a polymeric material selected from a hydrocarbon family. This layer placed in the closed proximity to the CMUT array exhibit an acoustic loss per millimeter for acoustic energy passing therethrough of less than 2 dB for a wide range of the acoustic wave frequencies applicable in medical ultrasound, such as in between 2 and 25 MHz. The layer of the thermoset elastomer having a polymeric material selected from the hydrocarbons has a density equal or below 0.95 $g/cm^3$ and an acoustic impedance equal or above 1.45 MRayl. When placed in a direct contact with the CMUT cell membrane the first layer provides an improved acoustical coupling of the acoustic window layer to the membrane of the CMUT cell. Thus, no additional coupling medium between the acoustic window and the CMUT array is required. The second layer comprising a thermoplastic polymer such as polymethylpentene provides a mechanical and chemical stability of the acoustic lens. The first layer comprising the thermoset elastomer has a first acoustic wave velocity (v1) and the second layer comprising thermoplastic polymer has a second acoustic wave velocity (v2) larger than the first acoustic wave velocity. This wave velocities difference in combination with the convex shape of the outer surface of the first layer provides a convergence of the acoustic waves generated by the CMUT array at a focal point of the acoustic lens. It is beneficial to have an acoustic lens comprising layers with the lowest possible acoustic wave attenuation. Polymethylpentene (TPX) material used as the second layer of the acoustic lens shows one of the lowest longitudinal acoustic wave attenuation among the thermoplastic polyolefins. It shows an acoustic loss per millimeter for acoustic energy passing therethrough of less than 3.5 dB for a wide range of the acoustic wave frequencies applicable in medical ultrasound, such as 2 to 10 MHz. Polymethylpentene is suitable for blending with polyolefin elastomers, which have higher attenuation for both the longitudinal acoustic wave and share wave. An introduction of the polyolefin elastomer into the blend with polymethylpentene changes the density of the blend. Since acoustic impedance of a material is proportional to the density of this material, the average impedance of the second layer may be tuned with the blended elastomer therein. Polymethylpentene provides the blend with mechanical, chemical stability and with low acoustic wave attenuation; whilst the polyolefin elastomer provides a possibility to tune the acoustic impedance of the blend and to further improve its acoustic wave propagation properties. If the second layer exhibits a low acoustic attenuation and reduced acoustic impedance that may be closer matched to the body, human tissue (about 1.6 MRayl). In addition the second layer comprising the polyolefin nature of the blend provides low water permeation levels. The second layer comprising this blend is resistant to disinfectants (used for typical medical ultrasound equipment); and has a good mechanical protective properties as impact and wear resistance and is bio compatible. The blend of polymethylpentene and polyolefin elastomer also provides an increased shear wave attenuation that beneficially reduces a cross talk between the transducer elements. Therefore, an application of such second layer may show a reduction of image artefacts during the ultrasound imaging.

In another embodiment of the present invention the elastomer includes polybutadiene.

It is beneficial to have an acoustic lens comprising layers with the lowest possible acoustic wave attenuation. Polybutadiene shows one of the lowest attenuation effects on the propagating acoustic energy. Polybutadiene material also provides a large band width of about 140% at 3 dB-point for the propagating acoustic signal. The acoustical coupling of this material to the CMUT array provides an optimal preservation of mechanical properties of the vibrating (moving) part of the CMUTs and results in the optimal acoustic energy propagation.

In a further embodiment the first layer including polybutadiene further comprises particles embedded therein for acoustic impedance adjustment of the first layer.

The introduction of the embedded particles into the polymeric material particles provides a possibility of increasing a total acoustic impedance of the first layer. This allows to tune the first layer's impedance closer to the acoustic layer impedance of the second layer.

Due to the fact that polybutadiene exhibits such a low acoustic energy loss (attenuation), possible additional acoustic losses caused by the embedded particles may be sufficiently low in order to influence a quality of the acoustic wave propagation through the acoustic window layer. When the first layer of the acoustic lens comprises polybutadiene with embedded insulating particles a direct acoustical coupling of the acoustical window layer to the membrane of the CMUT cell is provided. Thus, no additional coupling medium between the acoustic window and the CMUT array is required. In addition, due to the polymeric layer material's relatively low density and relatively high acoustic impedance, compared to silicon rubbers for example, a relatively smaller percentage by weight of the particles may need to be added for the further acoustic impedance adjustment such that the maximum acoustic impedance of the lens does not exceed a value of about 1.6 MRayl corresponding to the acoustic impedance of an ultrasonicated tissue.

In another embodiment the elastomer of the second layer is a thermoplastic elastomer comprising copolymer chains.

The outer acoustic layer of this embodiment would be a blend having thermoplastic properties. An example of the thermoplastic polyolefin elastomer (TPE) may be a copolymer of ethylene and another alpha olefin, such as octane or butane. In another embodiment of the present invention a percentage by weight of the particles based on the total weight of the first layer relates to the percentage by weight of the elastomer based on the total weight of the second layer, such that acoustic impedance of the first layer is substantially the same as the acoustic impedance of the second layer.

This embodiment allows a relative tuning of the acoustic impedances of the first and the second layers, while keeping the second wave velocity being larger than the first wave velocity. The percentages of the particles in the first layer and of the polyolefin elastomer can be selected such that the acoustic impedances of the two layers are matching (substantially the same). In this case the acoustic wave reflections at the interface of the two layers are minimized due to the matching acoustic impedance. Thus, the transmission properties of the acoustic lens, suitable for the acoustic waves converging, are improved. It is further beneficial to have the acoustic wave impedance of the lens to be close to the tissue impedance of about 1.6 MRayl.

In a further embodiment of the present invention the particles in the first layer include ceramic particles and the selected elastomer includes a copolymer having a first monomer being an alpha olefin, such as octane, and a second monomer being ethylene.

Ceramic particles are insulating and therefore can reduce often unwanted in medical application conductivity of the first layer. Olefin based copolymers are suitable for blending with polymethylpentene.

Yet another embodiment of the present invention the percentage by weight of the ceramic particles based on the total weight of the first layer is at most 25% and the percentage by weight of the elastomer based on the total weight of the second layer is at most 40%.

This embodiment provides improved conditions for the acoustic wave transition through the acoustic lens. Limiting the percentage of the particles to 25% and of the elastomer to 40%, preferably about 20%, provides a control over the wave's attenuation in the lens layers.

These and other aspects of the invention will be apparent from and elucidated with reference to the embodiments described hereinafter.

DETAILED DESCRIPTION OF EMBODIMENTS

Figure 1:
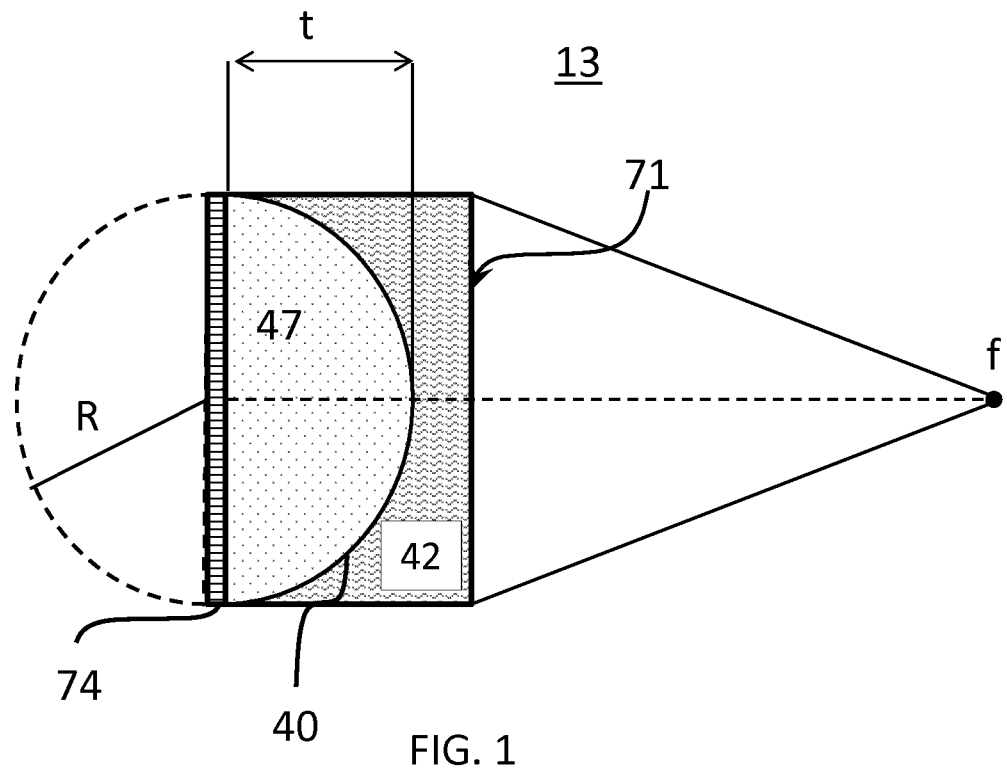
FIG. 1 shows schematically and exemplarily side view of an ultrasound array coupled to an acoustic lens suitable for acoustic wave converging.

FIG. 1 shows a principle of constructing a converging acoustic lens 13. The lens 13 is coupled to a source of the acoustic waves—an array of the capacitive ultrasound transducers 74. Further, the acoustic lens comprises a first layer 47 forming an inner layer, which is in an acoustic contact with the CMUT array, and a second layer 42 forming an outer layer of the lens. The first layer 47 has an inner surface arranged to face the array and outer convex shaped surface 40 arranged to oppose the inner surface of the first layer. The second layer coupled to the outer surface of the first layer may be forming an outer surface 71 of the acoustic lens 13. The outer surface is intended to face a patient 201 or a body to be examined by the ultrasound imaging system 202 (illustrated in FIG. 12).

When a speed of the sound or acoustic wave velocity varies from the first layer to the second layer of the acoustic lens a converging or diverging lens can be constructed. To illustrate in the first order approximation (all structures of the lens are large compared to the wavelength) a main principle of such a lens we use optical "lens maker formula". This formula gives a relation between a focal distance (f) of the lens and refractive index (n)

$$\frac{1}{f} = (n-1)\left(\frac{1}{R1} - \frac{1}{R2}\right)$$

wherein R1 is radius of curvature of the outer surface of the first layer relative to the CMUT array and R2 is radius of curvature of the second layer with respect to the CMUT array (in the present example this is the radius of the outer surface of the lens). In case of a planner outer surface of the lens, the lens maker formula can be presented as $$R1=R=(n-1)f \quad (1)$$

The refractive index of the lens is defined by a ratio of the acoustic wave velocities in the first (v1) and the second (v2) acoustic lens layers. When the second wave velocity is larger than the first wave velocity (v2>v1) the refraction index of the lens is greater than one.

$$n = \frac{v2}{v1} > 1 \quad (2)$$

Therefore, the acoustic lens coverages the acoustic waves at the focal point located at the focal distance (f) from the array.

A maximum thickness (t) of the first layer can be calculated as $$t=(1-\sqrt{3}/2)R \quad (3).$$

Figure 2:
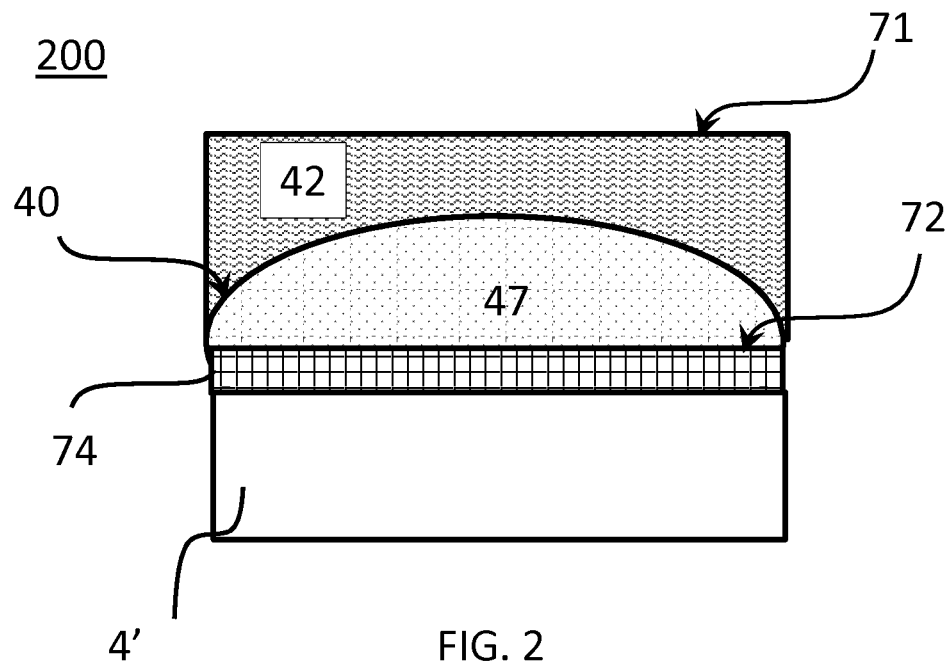
FIG. 2 shows schematically and exemplarily side view of an ultrasound probe comprising an ultrasound array of capacitive micromachined transducers and an acoustic lens having an first layer and second layer in accordance with the principles of the invention.
Figure 12:
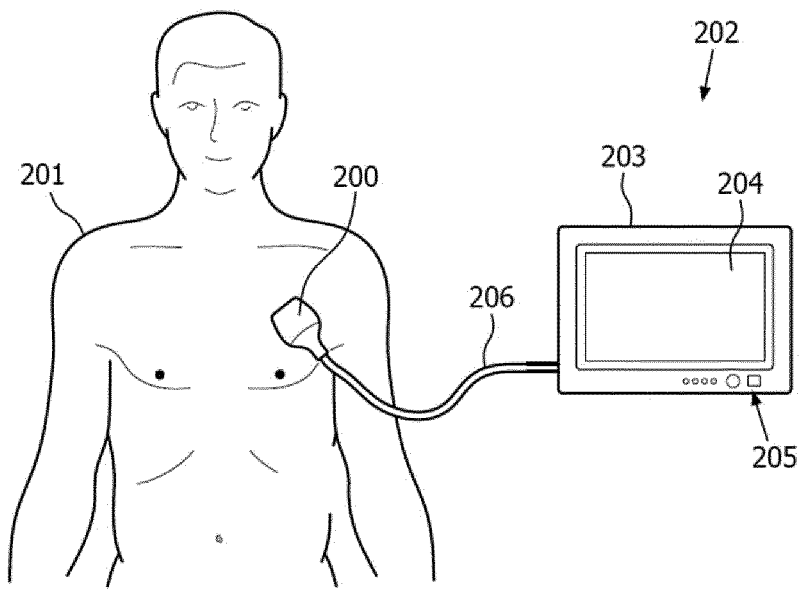
FIG. 12 shows a schematic illustration of an embodiment of an ultrasound imaging system.

FIG. 2 shows an ultrasound probe 200 according to the invention, comprising the CMUT array 74. The ultrasound array 74 has an ultrasound wave emitting side facing an inner surface 72 of an acoustic lens 13 (FIG. 1) and a backing side opposite to the emitting side. The CMUT array may contain ultrasound transducers coupled to an integrated circuitry adapted to drive and control the transducers in the array. The backing side of the array is electrically coupled to a probe's base 4', which communicates input and output signals of the integrated circuitry to and from an ultrasound system 202 (FIG. 12).

The acoustic lens 13 comprises a first layer 47 having the inner surface 72 arranged to face the CMUT array 74 and an outer convex shaped surface 40 arranged to oppose the inner surface; and a second layer 42 coupled to the outer surface 40 of the first layer 47. The first layer comprises a thermoset elastomer having a polymeric material selected from a hydrocarbon family. The thermoset elastomers are selected from hydrocarbons contain only hydrogen and carbon atoms and have a relatively low density (below 1 g/cm³). An application of the thermoset elastomers to the emitting surface of the CMUT array showed to provide an improved acoustic wave transmission through the first layer.

Most of elastomers are thermoset elastomers, which are generally characterized by wide-meshed crosslinking of the "knotted" molecular chains. This type of crosslinking means that the materials have a high level of dimensional stability but are still elastically malleable. By applying load (for instance tensile load) the chains become stretched, but after removal of the load they relax again. A typical hardness of the uncured elastomers is below 50 ShoreA, measured by a durometer (A scale). In general, cured (baked) elastomers exhibit higher hardness than 50 ShoreA. In order to keep the hardness below 50 ShoreA the elastomer comprising layer can be either under-cured (the solvent is not entirely evaporated as described in step) or/and have fatty acids added into a liquid mixture of the elastomer material. This will be discussed below in detail.

The individual molecular chains of the thermoset elastomers are characterized by three-dimensional closely meshed irreversible crosslinking. Thermoset elastomers are chemically and mechanically more stable among elastomers, thermoset elastomers may be processed similar to thermoplastics. Depending on the application a thermoset elastomer with different hardness can be selected. Uncured polybutadiene, for example, has a hardness of about 50 ShoreA, while butyl rubber, which polymeric chains consist of two monomers: isobutylene and isoprene, may show hardness values as low as 40 ShoreA. An olefin family (also alkenes) is a family of the unsaturated hydrocarbons comprising at least one carbon-carbon double bond.

The second layer 42 of the acoustic lens 13 comprises a polyolefin based thermoplastic polymer polymethylpentene. A polyolefin is a polymer comprising monomers selected from the olefin family. This layer further provides an efficient acoustic wave transmission through the acoustic lens by causing a reduced attenuation of the wave. When the first layer has a first acoustic wave velocity (v1) and the second layer has a second acoustic wave velocity (v2), which is exceeds the first acoustic wave velocity, the acoustic lens can be used for focusing the acoustic wave beams generated by the CMUT array.

Thermoplastic polymers are polymers in which, unlike thermoset elastomers, the molecular chains are not cross-linked. They consequently demonstrate plastic elastic behavior and are thermoformable (having the property of softening or fusing when heated and of hardening again when cooled). This formability is reversible, in other words can be repeated as often as required as long as the material is not thermally damaged by overheating. Since thermoplastics have little or no cross-linking their individual polymer chains can slip past one another on heating. In thermoplastic polyolefin, compared to the saturated hydrocarbons, the polyolefin family provides the thermoplastic polymer with a relatively light molecular weight. The thermoplastic polyolefin comprises linear isotactic polymers. In general thermoplastic polymers have a hardness of above 60 ShoreA.

Figure 4:
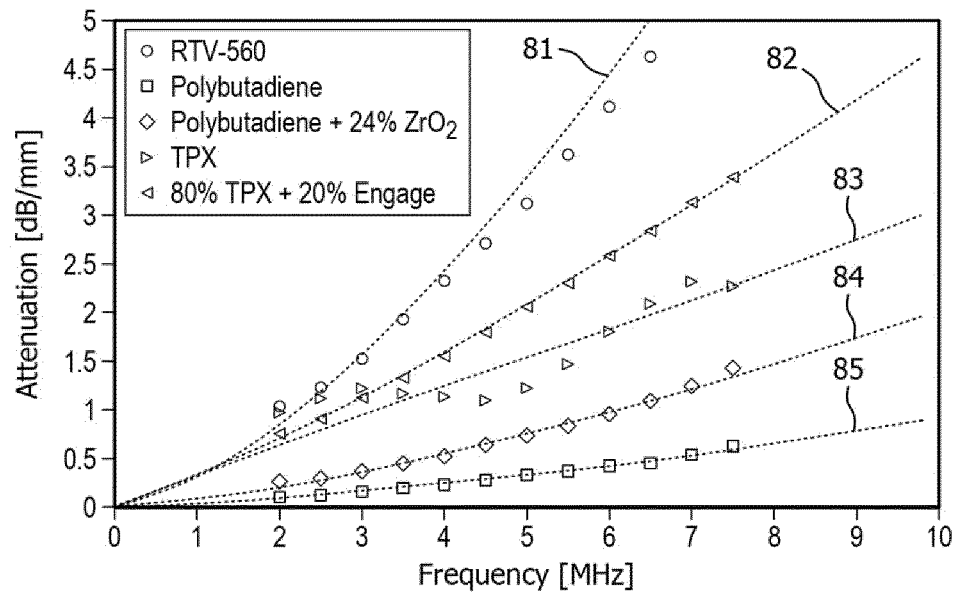
FIG. 4 is a graph comparing an acoustic frequency dependence of an acoustic loss (in dB) per millimeter for acoustic energy passing therethrough for different acoustic lens materials.

The preferred materials used in the lens for the first layer is polybutadiene and for the second layer is polymethylpentene. Polybutadiene and polymethylpentene (TPX) show one of the lowest attenuations for the acoustic wave in a broad range of frequencies. In FIG. 4 an acoustic frequency dependence of attenuation of the acoustic energy passing therethrough for different materials used in acoustic lens is shown. Symbols indicate measured data and lines indicate simulated dependencies. The presented materials show a steady increase of the attenuation value with the increase in frequency. The highest attenuation, which increases considerably with the frequency, is observed for the commonly used filled silicon rubber (RTV-560, curve 81): the attenuation reaches almost 5 dB/mm at a frequency around 7 MHz. The smallest attenuation is observed for polybutadiene (curve 85), which shows attenuation below 1 dB/mm at frequencies below 10 MHz. Compared to the RTV-560 a polymethylpentene material (curve 83) shows an improved attenuation varying from about 0.5 dB/mm at 2 MHz up to 3 dB/mm at 10 MHz. The blend of the TPX and Engage 8180 (an ethylene-octene copolymer available from Dow Chemical under trade name Engage) in the weight ratio of 80% and 20% shows an increased attenuation dependency compared to the pure polymethylpentene, however, this dependency is still improved compared to the commonly used filled silicon. The acoustic wave attenuation in the TPX/Engage 8180 (20%) blend changes from about 0.5 dB/mm at 2 MHz up to 4.5 dB/mm at 10 MHz.

The first layer including the polybutadiene material has acoustic wave velocity of about 1570 meters per second (m/s) and the second layer including the polymethylpentene material has acoustic wave velocity of about 2000 m/s. An application of these two materials in the acoustic lens provides a converging lens with minimized acoustic wave attenuation in a broad range of frequencies.

Figure 3:
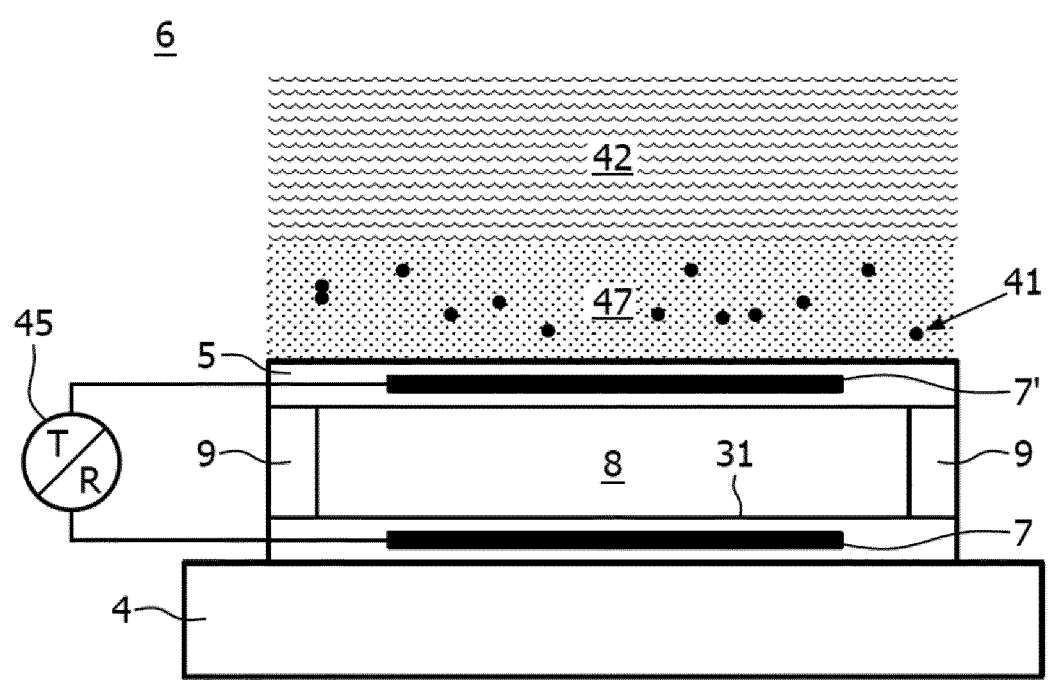
FIG. 3 shows schematically and exemplarily a side view of a CMUT cell of the ultrasound array and an overlaying lens comprising a first layer of polybutadiene with insulting particles embedded therein a second layer of polymethylpentene an elastomer selected from the polyolefin family (POE) blended therein.

An additional benefit of polybutadiene is that it is a suitable material for acoustic impedance matching. The polybutadiene material has acoustic impedance of about 1.45 MRayl. In order to minimize an impedance mismatch between the ultrasound array, the second layer and the ultrasonicated tissue it may be desirable to increase the acoustic impedance value of the first layer 47 comprising the polybutadiene. This can be achieved by adding a filler, such as insulating particles 41, into the first layer 47 (FIG. 3). The introduction of the insulating particles into polybutadiene increases a total density of the first layer. As has been already shown in FIG. 4, the additional acoustic losses caused by the embedded insulating particles are sufficiently low and do not considerably influence a quality of the acoustic wave propagation through the first layer.

As an example, Table 1 shows the measured changes in acoustic properties of the polybutadiene layer with the introduction of zirconium dioxide ($ZrO_2$) insulating particles having in average diameter of 2-3 micron and taking a fixed percentage of a total weight of the inner layer.

TABLE 1

Changes in the density, acoustic wave velocity, acoustic impedance and attenuation (at frequency of 7 MHz) with an increasing weight percentage of $ZrO_2$ particles in the total weight of the polybutadiene layer.

| % ZrO2 | Density (g/cm$^3$) | Velocity (m/s) | Impedance (MRayl) | Attenuation @7 MHz (dB/mm) |
|---|---|---|---|---|
| 0 | 0.906 | 1570 | 1.423 | 0.55 |
| 4% | 0.937 | 1553 | 1.455 | 0.75 |
| 8% | 0.972 | 1532 | 1.489 | 0.87 |
| 16% | 1.0405 | 1503 | 1.564 | 1.05 |
| 24% | 1.0855 | 1469 | 1.5945 | 1.25 |

As can be seen from the table with the total density increase of the first layer comprising polybutadiene, the acoustic impedance of the first layer can be tuned towards higher values, while the attenuation of the layer still remains below 1.5 dB/mm, even for the layers comprising 25% of its weight taken by the insulating particles ($ZrO_2$). As can be seen from the table together with addition of the particles both the acoustic impedance of the material and wave velocity of the sound wave traveling through this material can be varied.

Acoustic impedance (Z) of a material is defined as the product of acoustic propagation velocity (v) for acoustic energy (or wave) in a medium and density (ρ) of this medium:

$$Z = \rho * v.$$

Therefore, changing the density of the material allows tuning its acoustic impedance and acoustic wave velocity, as can be also seen from Table 1 for the polybutadiene material.

When the first layer of the lens, comprising the polybutadiene with embedded insulating particles, has a density equal or above 0.94 g/cm$^3$ and an acoustic impedance equal or above 1.5 MRayl a direct acoustical coupling of the acoustical window layer to the membrane of the CMUT cell is provided. Thus, no additional coupling medium between the acoustic window and the CMUT array is required. Moreover, the acoustic impedance equal or above 1.5 MRayl matched closer to the values in between the CMUTs acoustic impedance and the tissue.

Thermoset elastomers selected from a hydrocarbon family have light molecular weight compared to commonly used in ultrasound silicon based rubbers (filled silicon). These elastomers, in particular polybutadiene, possess higher acoustic impedance. Therefore, in order to increase their impedance a relatively smaller amount of the filler may be used in this polymeric material, compared to the filled silicones. Since an introduction of the insulating particles to a layer on average increases its hardness, an application of the polybutadiene having higher acoustic impedance provides the first layer with relatively smaller changed hardness and a considerably lower attenuation (preferably below 1.5 for frequencies below 20 MHz or 2 dB/mm for frequencies in between 20 and 25 MHz) than with filled silicones. In contrast, in order to increase the acoustic impedance of the filled silicon closer to the soft tissue's impedance, i.e. from 1.1 MRayl to 1.6 MRayl, a larger amount of the filler particles is required. This introduction of the particles causes a considerable attenuation and increase in the hardness of the filled silicon layer.

Following, ceramic particles as fillers (insulating particles) may be used: ZrO2, Al2O3, TiO2, Bi2O3 and BaSO4 (species of metal oxides). Ceramic particles show high insulating properties, which may be advantages in providing additional insulation to the arrays electronics. Moreover, there are multiple ways developed in the art for manufacturing ceramic particles of a well-defined size. The reduced acoustic wave attenuation in the layers of polybutadiene and polybutadiene having 24% of the layer's total weight filled with $ZrO_2$, particles can be seen from the curves 84 and 85 in FIG. 4 respectively. The polybutadiene with embedded insulating particles shows attenuation below 2 dB/mm at 10 MHz and below 1 dB/mm at 5 MHz.

Similar to polybutadiene the polymethylpentene (poly 4-methyl pentene-1) material used in the second layer provides an advantage of acoustic impedance tuning of the second layer. Polymethylpentene (available from Mitsui under trade name is TPX) material shows a low longitudinal acoustic attenuation as can be seen from FIG. 4 curve 83. In this context the longitudinal attenuation corresponds to the wave's amplitude reduction while propagating from the inner surface arranged to face the array the outer surface. The TPX material has relatively low density, while due to its hardness exhibiting relatively high acoustic wave velocity (above 2 mm/msec). Compared to other more dense polymers with similar acoustic wave velocities, the TPX has relatively high acoustic wave velocity, while showing relatively low acoustic impedance of about 1.7 MRayl. However, as has been already indicated above that the TPX material has low shear wave attenuation. In contrast to the emitted ultrasound waves propagating from the ultrasound array throughout the lens 13 towards the patient, the shear wave travels along the acoustic window surface and increases the cross talk between the transducers affecting the ultrasound image quality. It may be also desired to bring the impedance of the second layer closer to the tissue impedance.

It was shown that the introduction of a polyolefin elastomer (POE) into the blend of the polyolefin thermoplastic polymer (polymethylpentene) allows reducing the impedance of the blend (while increasing its density), which permits tuning acoustic properties of the second layer. In addition it was also found out that this blend has an increased shear wave attenuation that beneficially reduces a cross talk between the transducer elements in the array 74. Therefore, the ultrasound probe 200 having the acoustic lens 13 with the second layer 42 formed from a blend of the polymethylpentene and polyolefin elastomer may show a reduction of image artefacts during the ultrasound imaging.

Blending (compounding) of these polymer materials can, for instance, be performed with a twin screw extruder. The blend of the thermoplastic polymer and the elastomer represents a so called immiscible polymer blends (heterogeneous polymer blends), wherein the blend made of these two polymers exhibits two sets of distinct physical properties, such as glass transition temperatures and melting point, corresponding to the materials forming the blend. An additional advantage of the polyolefin elastomer that it is compatible with most olefinic materials, where in olefinic is any of a class of unsaturated open-chain hydrocarbons having at least one double bond. Most commercially available polyolefin based elastomers (POEs) are copolymers of either ethylene-butene or ethylene-octene. It shall be noted that blending provides a homogenous distribution of the thermoplastic and elastomer materials within a given volume, without a formation of separate islands of different materials, wherein said islands can introduce additional sources of scattering for the ultrasound waves.

In a further example, the polymethylpentene material is blended with another type of elastomers: a thermoplastic elastomers (TPEs), which are as well as general thermoplastics mentioned above have no or little crosslinking. The thermoplastic elastomers can be copolymers, wherein the high level of thermoplastic elastomer dimensional stability and their elastic malleability is achieved by combining in one two different types of polymers. TPEs provide a material with an ability to be stretched to moderate elongations and return to its near original shape creating a longer life and better physical range. Most commercially available TPEs are polyolefin copolymers of either ethylene-butene or ethylene-octene.

In another aspect of the invention the second layer of the lens comprises a blend of polymethylpentene and a copolymer forming the polyolefin elastomer. Copolymers are a physical mix of polymers (two different monomers) which consist of materials with different elastic properties. The copolymer of the polyolefin elastomer is a copolymer of ethylene and alpha olefin such as octane or butane. Alpha-olefins (or α-olefins) are a family of organic compounds which are alkenes with a chemical formula $CnH_{2n}$, distinguished by having a double bond at the primary or alpha (α) position. In another embodiment, the outer layer comprises a blend of polymethylpentene and ethylene-octene copolymer. This copolymer is available from Dow Chemical under trade name Engage.

The ethylene-octene copolymer is suitable for blending with polymethylpentene due to its olefin nature. This copolymer exhibits on average lower, than the TPX, acoustic impedance and almost an order of magnitude higher shear wave attenuation. The resulting blend of the TPX and ethylene-octene copolymer inherits from the TPX the reduced density with relatively high acoustic wave velocity; and from the copolymer reduced acoustic impedance and increased shear wave attenuation. Therefore, an improved outer layer 42 comprising the blend from the TPX and the ethylene-octene copolymer can be obtained. This blend provides the window layer of the acoustic probe with durability and low acoustic attenuation properties next to the improved imaging quality due to the reduced image artifacts originating from the window layer.

Table 1 shows a comparison of the acoustic properties measured for different materials: polymethylpentene (Mitsui TPX MX0002, having 4 monomers in a polymer chain), polyolefin elastomer (Engage 8180 having 4 monomers in a polymer chain); two blends of the polymethylpentene (TPX MX0002) and polyolefin elastomer (Engage 8180), wherein an amount of the elastomer in the blend 15% and 20% of total blend's weight correspondingly.

TABLE 2

Changes in material's parameters of different layer materials: density, acoustic wave velocity, acoustic impedance, acoustic energy attenuation (at the acoustic wave frequency of 7 MHz) and shear wave attenuation.

| Layer material | Density (g/cm³) | Velocity (mm/msec) | Impedance (MRayl) | Attenuation @7 MHz (dB/mm) | Shear wave Attenuation (dB/mm) |
|---|---|---|---|---|---|
| Engage 8180 | 0.874 | 1622 | 1.417 | 4.51 | >17 |
| TPX/Engage (15%) | 0.835 | 1923 | 1.607 | 2.71 | 5 |
| TPX/Engage (20%) | 0.832 | 1899 | 1.580 | 3.12 | 10 |
| TPX | 0.819 | 2067 | 1.692 | 2.31 | 1 |

Engage 8180 has the lowest density from the commercially available Engage types. Engage 8180 material shows a considerable attenuation of the shear wave (above 17 dB/mm) in addition it also shows the relatively high acoustic wave attenuation increasing from about 1.5 dB/mm at 2.5 MHz up to 5 dB/mm at 7.5 MHz. The blend of TPX and Engage 8180, wherein a weight ratio of 85% and 15% correspondingly, compared to the TPX, shows a slight increase in density up to 0.835 gram per cubic centimeter (g/cm³) with an improved shear wave attenuation of about 5 dB/mm and an increased acoustic wave attenuation being about 2.71 dB/mm at 7.5 MHz. The acoustic impedance of the TPX and Engage 8180 (85/15%) blend is reduced down to 1.6 MRayl, compared to the TPX material, which brings acoustic impedance value of the outer layer 42 closer to the tissue impedance. The share wave attenuation of the blend can be further improved (increased) by increasing the weight ratio of the Engage in the blend. In case of the blend of TPX and Engage 8180, with the corresponding weight ratio of 80% and 20%, the shear wave attenuation may be as high as 10 dB/mm with the acoustic impedance further reduced to 1.58 MRayl. These improvements may be balanced by a slight increase in the acoustic wave attenuation energy value of about 3.12 dB/mm at 7 MHz.

The blending of these polymers provides a freedom of varying the acoustic wave velocity of the blend by changing the weight ratio of the polymers in the blend depending on different medical applications.

Thus, the second layer 42 formed from blend of thermoplastic olefin (polymethylpentene) and polyolefin elastomer (ethylene-octene copolymer) exhibits a low acoustic attenuation and reduced acoustic impedance that may be closer matched than the first layer 47 to body/human tissue. In addition, when the second layer forms the outer surface of the lens 13, the second layer 42 provides low water permeation levels and lens improved resistant to disinfectants (used for typical medical ultrasound equipment). This property is attributed the fact that both components forming the blend are olefin based making the blend non-polar, therefore, chemically stable towards the disinfectant treatment commonly used for medical devices. The lens 13 comprising the second layer from the polymethylpentene blend also shows good mechanical properties (with respect to an impact and wear resistance).

Figure 5:
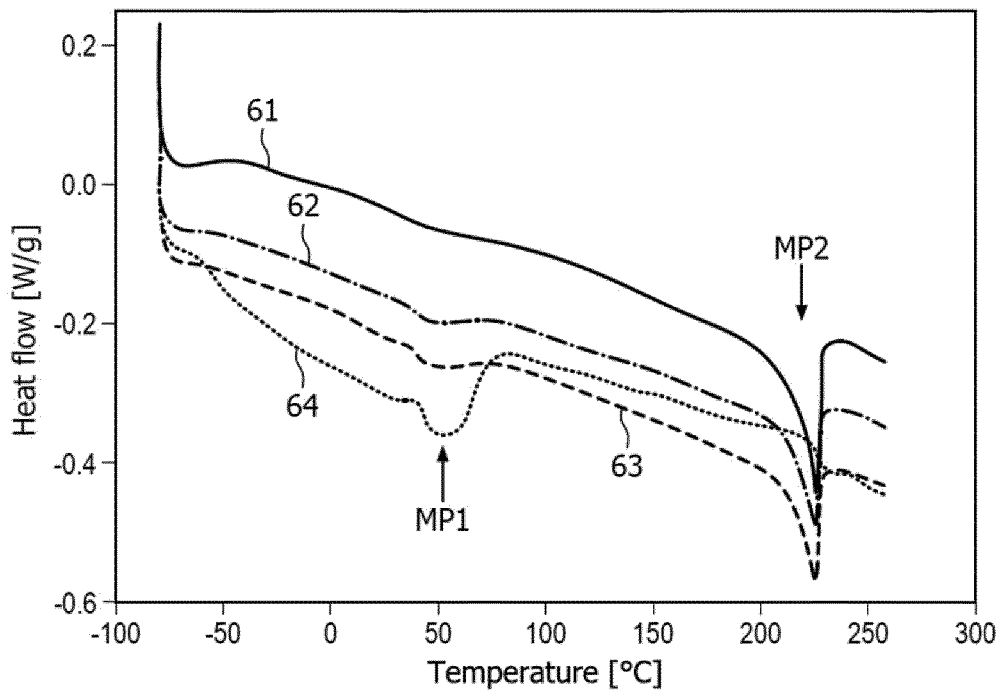
FIG. 5 shows comparison between the differential scanning calorimetry curves for polymethylpentene, polyolefin elastomer and different concentration blends of polymethylpentene with polyolefin elastomer.

In order to characterize the obtained blends the differential scanning calorimetry and dynamic mechanical analyses may be performed. FIG. 5 shows the differential scanning calorimetry curves for polymethylpentene (TPX MX0002, curve 61); polymethylpentene/polyolefin elastomer blends (TPX/Engage 8180) having the weight ratio of 80%/20% (curve 62) and 85%/15% (curve 63) correspondingly; and polyolefin elastomer (Engage 8180, curve 64).

As can be seen from the curves 62 and 63, the heat flow temperature dependence has two extrema points around 50 and 225 centigrade Celsius. This indicates that the blend of the polymethylpentene with the polyolefin elastomer exhibits two melting points, wherein the lowest temperature point represents a first melting point (MP1) in between 30 and 70 centigrade Celsius associated with the polyolefin elastomer (compared to the curve 64) and the highest point represents a second melting point (MP2) in between 200 and 250 centigrade Celsius associated with the thermoplastic polymer (compared to the curve 61). Indeed, heat flow curves of pure Engage 64 and TPX 61 have one extreme point each: around 50 centigrade Celsius corresponding to the polyolefin elastomer (Engage, 64) and around 225 centigrade Celsius corresponding to thermoplastic polymer (TPX, 61).

Figure 6:
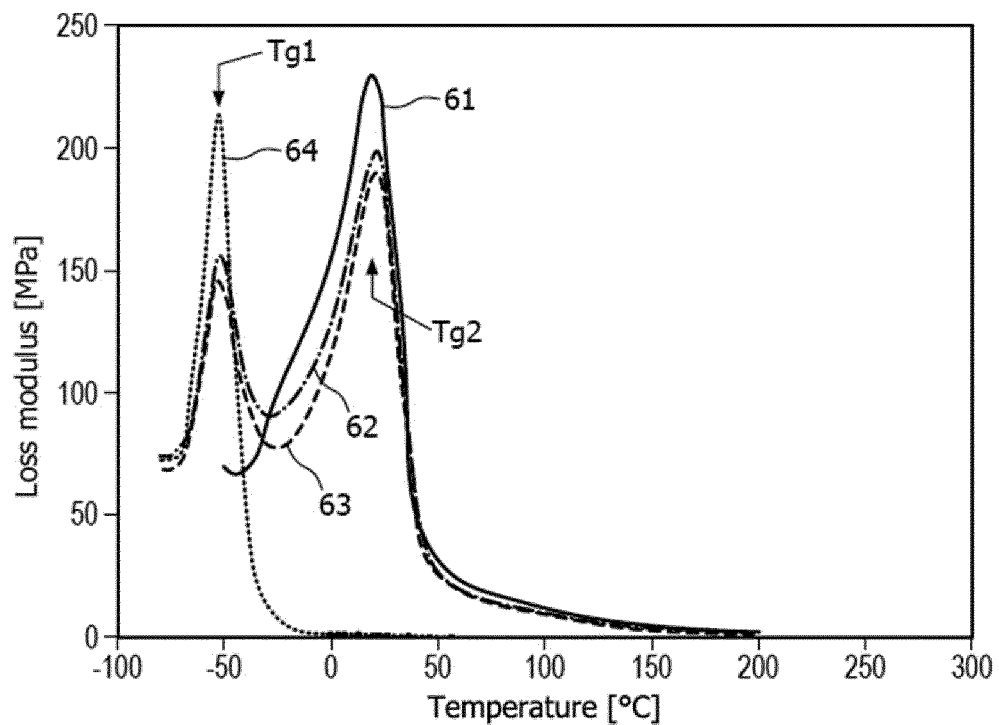
FIG. 6 shows comparison between the dynamic mechanical analyses curves for polymethylpentene, polyolefin elastomer and different concentration blends of polymethylpentene with polyolefin elastomer.

FIG. 6 shows the dynamic mechanical analyses curves for the same set of materials. For simplification the same reference numbers are used in both figures: FIG. 5 and FIG. 6. The loss modulus temperature dependence of the blends (curves 63 and 63) shows two extrema combining the properties of both blended materials. The maximum below −40 centigrade Celsius, in particular around −60 centigrade Celsius, is a first glass transition temperature (Tg1) corresponding to the polyolefin elastomer, in particular Engage. The maximum between 0 and 50 centigrade Celsius, in particular around 25 centigrade Celsius, is a second glass transition temperature (Tg2) corresponding to the thermoplastic polyolefin, in particular TPX. The loss modulus curves of pure Engage 64 and TPX 61 have one extreme point each: around −60 centigrade Celsius corresponding to the elastomer (Engage, 64) and around 25 centigrade Celsius corresponding to thermoplastic polyolefin (TPX, 61).

In accordance with the invention the ultrasound array 74 comprises at least one CMUT cell as shown in FIG. 3. Such CMUT cell is typically fabricated on a substrate 4, such as a silicon wafer. This substrate may be located within the base 4' of the probe 200 in FIG. 2. An ultrasound array 74 of an ultrasound probe 200 may comprise one or more CMUT cells 6. The CMUT cells may be either individually activated or in combination with each other. The individual cells can have round, rectangular, hexagon or other peripheral shapes.

Each CMUT cell has at least a pair of electrodes 7' and 7 separated by a cavity 8. The cavity 8 is formed in between a membrane 5 that is suspended over a cell floor 31 formed by the top surface of the substrate 4. The membrane 5 may be made of silicon nitride and is adapted to move or vibrate. It can be suspended over the cell floor 31 (or substrate) through a plurality of supporting portions 9 (in FIG. 2 two supporting portions 9 are shown). The electrodes 7, 7' are made of electrically conductive material, such as metal. The bottom electrodes 7 may be embedded in the floor of the cell 31, while the top electrode 7' may be embedded in the membrane 5. The electrode 7 and 7' may be also deposited on the cell floor 31 or the membrane 5 as additional layers. The bottom electrode 7 is typically insulated on its cavity-facing surface with an additional layer (not shown). This insulating layer can comprise either one of or a combination of an oxide-nitride-oxide (ONO) dielectric layer, silicon oxide layer, aluminium or hafnium oxide layers. The insulating layer may be formed above the bottom electrode 7 and below the membrane electrode 7'. The ONO-dielectric layer advantageously reduces charge accumulation on the electrodes which leads to device instability, drift and reduction in acoustic output pressure. The supporting portions 9 may be made of an insulating material such as silicon oxide or silicon nitride. The cavity 8 can be either air- or gas-filled, or wholly or partially evacuated. Two electrodes 7 and 7' separated by the cavity 8 represent a capacitance. An application of electrical signal through a drive circuit 45 coupled to the electrodes 7 and 7' causes a mechanical movement/vibration of the membrane 5, which results in the change of the capacitance and can be manipulated by an associated with the CMUT transducer integrated circuitry. The drive circuit 45 can be implemented as an integrated part of the integrated circuitry of the ultrasound array. The drive circuit 45 usually comprises an a.c. signal voltage and a d.c. voltage sources and associated to these sources circuitry.

A conventional PZT-based transducer typically has a parallelepiped shape, wherein at least one of its faces is adapted to vibrate in a piston-like motion during the transmission of the acoustic wave. The displacement of the vibrating (active) face is homogeneous throughout the face surface.

Figure 8:
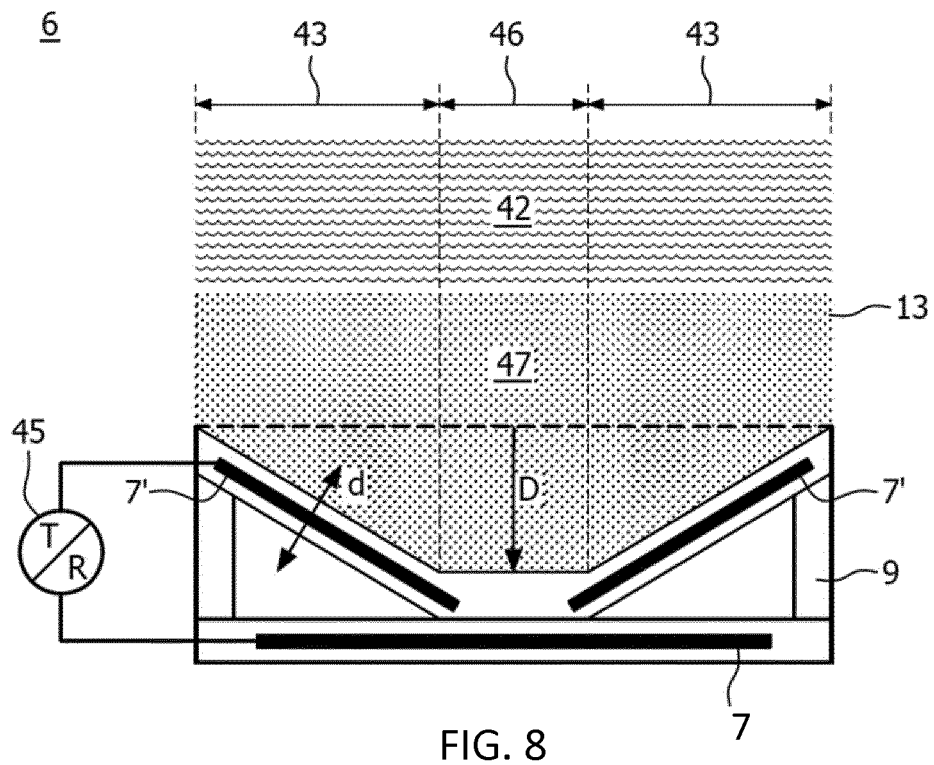
FIG. 8 shows schematically and exemplarily a side view of a CMUT cell operating in the collapsed mode and being acoustically coupled to an acoustic lens.

In contrast, the CMUT's vibrating membrane has a different displacement throughout the membrane's area (surface). In a conventional operation mode the membrane's displacement is highest in the central part of the CMUT cell and lowest at the periphery of the membrane. In a collapsed mode of operation as shown in FIG. 8 the membrane 5 of the CMUT cell 6 is partially contacting the cell floor, which results in the biggest membrane displacement (D) compared to the conventional operation mode. During the CMUT operation a central part of the membrane 46 may be brought into the contact with (collapsed to) the cell floor by applying a collapsed d.c. voltage value (the d.c. voltage is supplied by the drive circuitry 45). The applied a.c. signal voltage supplied by the drive circuitry 45 causes the suspended portions of the membrane 43 (located at a periphery of the membrane) to move/vibrate under applied electrical signal in between electrodes 7 and 7'. From technology point of view, the CMUT with the collapsed membrane can in principle be manufactured in any conventional way, comprising providing a CMUT with a membrane and applying different means, such as electrical (bias voltage) or pressure, in order to bring the membrane to a collapsed state. In the collapsed operation mode, the displacement D of the central part of the membrane is fixed, while the suspended portions of the membrane vibrate with an amplitude d, which is determined by the a.c. voltage signal for the given CMUT cell design.

The variation in the displacement of the membrane's vibrating portions imposes different requirements on the lens layer being acoustically coupled to the CMUT array in order to provide an improved acoustic coupling of the operating CMUT transducer. The layer forming an acoustical contact with the CMUT may need to adopt its inner surface to the membrane's displacement. The relatively light molecular weight of the polybutadiene combined with its relatively low hardness (below 60 ShoreA, preferably below 50 ShoreA) may provide an improved acoustic contact between the acoustic window layer 13 and the CMUT's membrane adapted to vibrate. In addition the low acoustic wave attenuation of the material forming the inner layer may provide an improved transition of the wave throughout the lens 13.

The acoustic lens of the present invention may comprise the first layer 47 including the thermoset elastomer having a polymeric material selected from a hydrocarbon family, such as polybutadiene, and insulting particles embedded therein; and the second layer 42 comprising the thermoplastic polyolefin (TPO), such as polymethylpentene, and elastomer selected from the polyolefin family (POE) blended therein for acoustic impedance adjustment.

The CMUT array is preferably arranged to operate in the collapsed mode by comprising at least one drive circuit 45 coupled to the CMUT cell 6 and adapted to (a) bring the membrane 5 into a collapsed state in which the membrane is collapsed to the substrate 4, by applying a d.c. voltage over the first 7 and the second electrodes 7' of the at least one CMUT cell, and (b) activate the CMUT cell by applying an a.c. voltage over the first and the second electrodes of the at least one said CMUT cell.

In this mode the CMUT ultrasound array may transmit or receive ultrasound acoustic at different frequencies by varying the applied d.c. voltage, which in return changes the contact area of the membrane 5 with the substrate 4. The larger the d.c. voltage the larger the contact area in the collapsed mode and the higher the resonance frequency of the CMUT cell. Therefore, compared to the PZT-based array the CMUT-based ultrasound array may impose additional requirements onto the acoustic lens 13 in order to provide improved acoustic wave propagation for a large frequency range, in which the CMUT ultrasound array is adapted to operate. Therefore, it is desirable to have both the first 47 and the second 42 layers showing reduced acoustic wave attenuation within the broad band of the operating frequencies.

Figure 7:
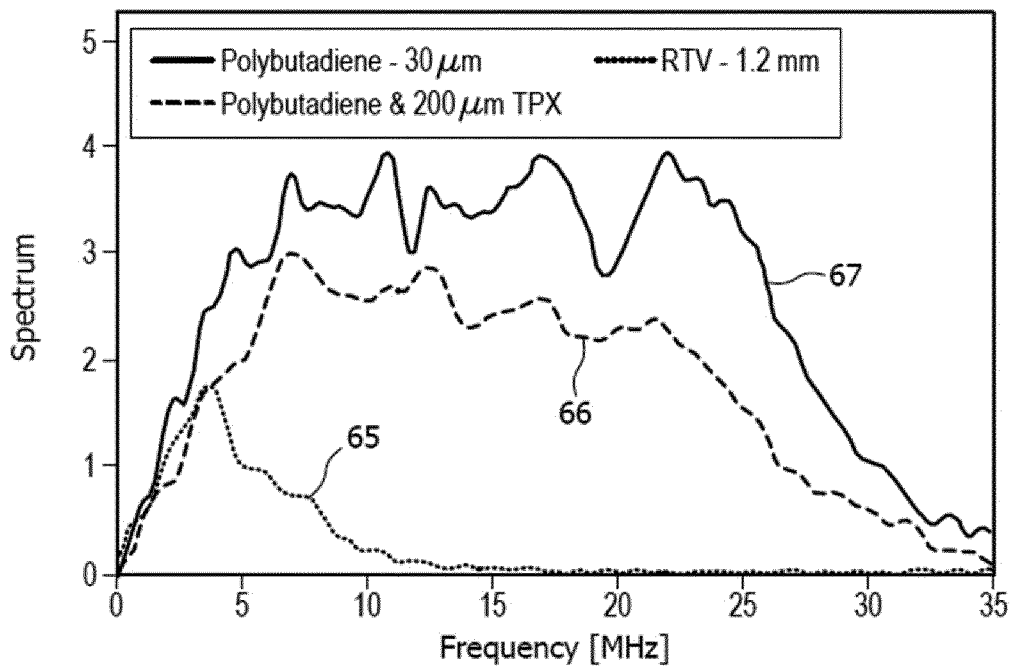
FIG. 7 shows comparison of an output pressure of the CMUT array comprising an acoustic window layer having different materials forming the outer and inner layers.

FIG. 7 shows an output pressure (MPa) in the frequency range from 0 up to 35 MHz for the CMUT ultrasound array acoustically coupled to layers of different materials. Curve 65 corresponds to the ultrasound array overlaid by a common for the PZT application filled silicon rubber (RTV) of 1.2 millimeter in thickness. As can be seen the silicon rubber layer has poor performance for the CMUT array in this range of frequencies manifesting in the low output pressure reaching its maximum of 1.5 MPa around 5 MHz; beyond frequencies of 7 MHz the filled silicon rubber exhibits a strong attenuation of the acoustic signal. The CMUT array overlaid by the first layer comprising polybutadiene material (curve 67) having a thickness of 30 micrometer shows an ultra-wide bandwidth with an output pressure reaching as high as 3.5 MPa. Curve 66 corresponds to the acoustic window layer 13 comprising both the first layer 47 formed by polybutadiene (30 micrometer thick) and the second layer 42 formed by polymethylpentene having a thickness of 200 micrometer. The output pressure for this array reaches as high as 2.5 MPa and is above 2 MPa in a broad frequency range from 7 up to 22 MHz. Thus, present invention provides a converging acoustic lens with improved acoustic wave transmission and the wide frequency bandwidths, characterized with low acoustic wave attenuation, combined with the durable and cleanable outer surface 71 of the lens 13.

Figure 9:
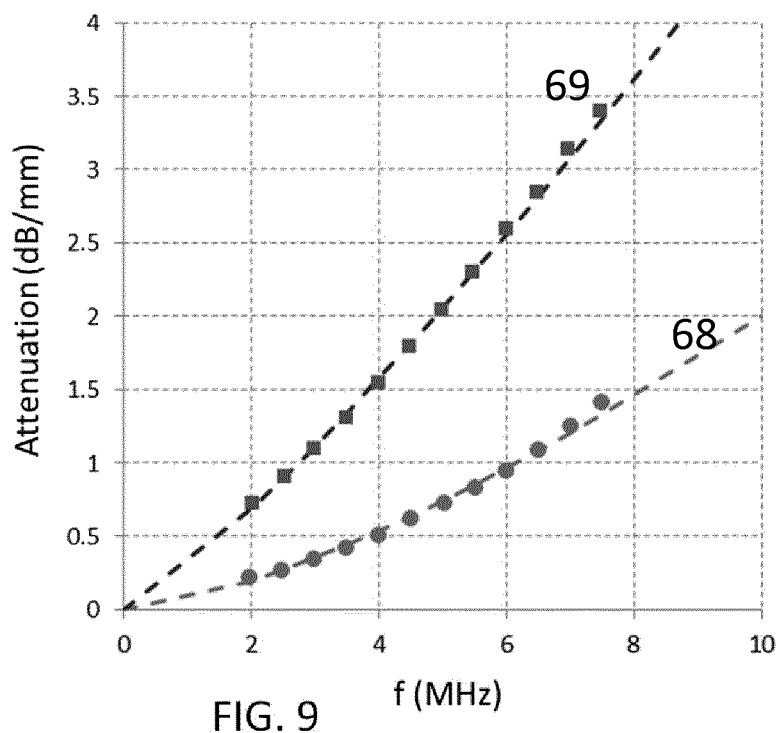
FIG. 9 shows a comparison of an acoustic frequency dependence of an acoustic loss (in dB) per millimeter for acoustic energy passing through the first layer of polybutadiene comprising 25% of $ZrO_2$ particles embedded therein and through the second layer comprising a blend of polymethylpentene with 20% of Engage.

The acoustic properties of the first and the second layers can be further adjusted by varying the weight ratios of the embedded insulating particles the blend component. FIG. 9 illustrates an example of the acoustic impedance matching, which can be implemented in the present invention. Curve 68 shows the acoustic frequency dependence of the acoustic loss (in dB) per millimeter for acoustic energy passing through the first layer of polybutadiene comprising 25% of $ZrO_2$ particles embedded therein (filled circles indicate measured data); and 69 shows the same dependence of the acoustic loss for acoustic energy passing through the second layer comprising a blend of polymethylpentene with 20% of Engage (filled squares indicate measured data). Both layers exhibit losses below 3 dB/mm for frequencies below 7 MHz, said frequency range comprises a region for general imaging in ultrasound diagnostic application. The percentage of $ZrO_2$ particles in polybutadiene relates to the percentage of Engage in the polymethylpentene blend such that the acoustic impedances of both layers are about the same 1.6 MRayl. This provides virtually no interface (due to the same impedance values) in between the first and second layer for the acoustic energy traveling therethrough. Thus, the reflection of the acoustic waves at the boundary of the lens layers is minimized. The density value of polybutadiene comprising 25% of $ZrO_2$ is about 1.09 $g/cm^3$, while the acoustic wave velocity is about 1470 m/s; the density value of the polymethylpentene blend comprising 20% of Engage is about 0.8 $g/cm^3$, while the acoustic wave velocity is about 1900 m/s. One can calculate a required radius of curvature for the convex surface 40 of the first layer of the lens in accordance to this embodiment. In the first order approximation (for 5 MHz the wavelength is about 0.3 mm in this materials) referring to formulas (1) to (3) for a typical focal length of 5 cm the refraction index of the lens 13 is 1.29 and the curvature radius of the convex surface 40 is 1.5 cm, with maximum thickness of the first layer being 1.5 mm. The maximum thickness (t) and the curvature radius (R) would change with the size of the array (probe's aperture size).

Figure 10:
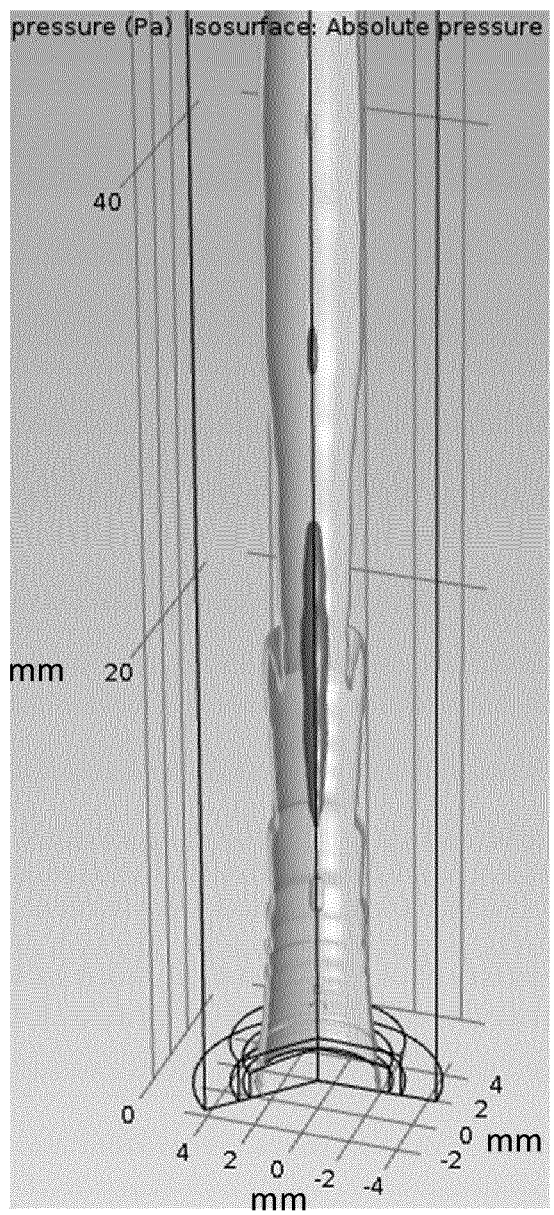
FIG. 10 illustrates a simulation of spatial acoustic pressure distribution of the CMUT array coupled to the acoustic lens constructed in accordance to the present invention.

FIG. 10 gives a full acoustical wave analyses (spatial pressure distribution generated by the probe in Pascal units) in a broad range of frequencies for the lens constructed in accordance to the example above. The total thickness of the lens is 2 mm, 1.5 mm of which is the maximum thickness of the first layer. The curvature radius of the convex shaped surface of the first layer with polybutadiene is 1.3 cm. Without the lens, a natural focus of this array is at about 1.7 cm. An application of the lens to the array enhances focusing and the focal point is shifted to larger distances of 2.5 cm. Increasing a total thickness of the lens may further improve focusing (at the cost of increased attenuation). For example, with an accepted attenuation level using the same 1.3 mm radius of curvature, the thicker lens move can move the focal point to 3.0-3.5 cm, which comes closer to the first order approximation discussed above.

The CMUT based arrays may find their common application is ultrasound imaging based disposable products, such as interventional ultrasound probe's or on body patches. These applications have stricter requirements with respect to the sterility. The application of the second layer comprising the thermoplastic polymer polymethylpentene and the elastomer selected from the polyolefin family (POE) blended therein enables the focusing function of the acoustic lens, while also providing said lens with mechanical and chemical stability making an ultrasound device having such a lens suitable for the sterilization with common chemicals.

An additional benefit of the present invention is that suggested layer materials are moldable and can be easier adapted to industrial manufacturing of the ultrasound probes.

Figure 11:
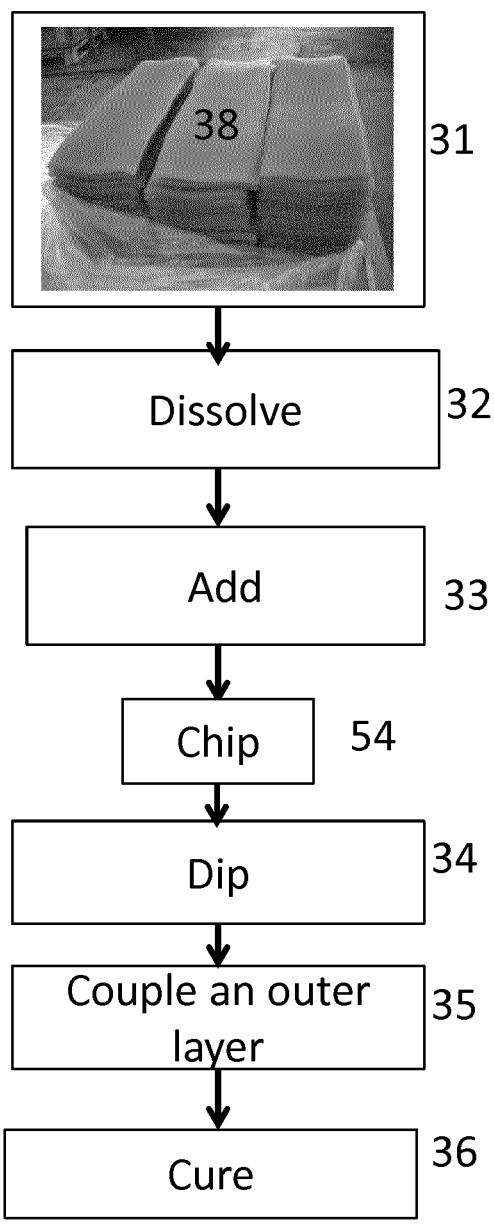
FIG. 11 schematically illustrates a method for manufacturing an ultrasound array in accordance with the present invention.

In FIG. 11 a method 20 for manufacturing an ultrasound array comprising the acoustic lens in accordance with the present invention is illustrated. A granulate of pre-polymerized polybutadiene 38 (CB728T from Lanxess) is provided in step 31. In step 32 the block is granulated and dissolved in solvents like alkanes, branched or cyclic alkanes, for example hexane, heptane, cyclohexane. In step 33 the optimization of the acoustic impedance of the first layer can be achieved by adding insulating particles to the solvent, wherein the polymeric material act as a dispersion agent for the particles, such that a liquid mixture of the polymeric material and the insulating particles is provided. The additional dispersion agents like fatty acids (a carboxylic acid with an aliphatic chain, which is either saturated or unsaturated) may be added in the liquid mixture. The filler particles in the liquid mixture may increase the hardness of the inner layer of the acoustic window, while fatty acids may counter play this hardness increase keeping the average hardness of the first layer at the relatively constant value. The unsaturated chains of fatty acid like oleic acid, linoleic acid and linolenic acid (one, two and respectively tree double carbon bonds) can polymerise and bond to the polybutadiene chains. This provides a good dispersion/distribution of particles in the liquid mixture. In step 54 a chip having the ultrasound array with at least one CMUT cell coupled to an integrated circuitry is provided. In step 34 the chip is dipped in the liquid mixture, such that a layer comprising the liquid mixture overlays the CMUT cell. Since in step 33 a minimum impedance mismatch between the liquid mixture and the propagating medium can be achieved, the tolerance to the thickness variation of the liquid mixture layer is rather high. The increase in the dipping time would increase the thickness of the liquid mixture layer. At this stage the desired curvature shape of the outer surface of the first layer is introduced. In the step 35 the chip with the liquid mixture layer may be let drying at elevated temperature of about 70° C. With the time, when the solvent starts evaporating from the liquid mixture, the liquid mixture layer may become more solid (sticky). At this stage the second layer of the polyolefin thermoplastic with the polyolefin elastomer blended therein is applied to the liquid mixture layer. The advantage of this step is that the second layer can be coupled to the first layer without any glue.

The preferred weight ratio of the polyolefin elastomer in the blend of the thermoplastic polyolefin is below 40%. For the embodiment describing polymethylpentene (TPX) with polyolefin elastomer blended therein (Engage), the elastomer's weight ratio increase beyond 40% introduces too high attenuation in the outer layer. Below 40% an optimal balance between the decreased acoustic impedance, reduced shear wave propagation and increased acoustic wave attenuation is achieved. The preferred weight ratio of the polyolefin elastomer in the thermoplastic polyolefin blend is in between 10% and 30%, in particular in between 15% and 20%. The exact value of the selected weight ratio of both blend components and particles may depend on the medical application of the ultrasound array. For example, for low frequency applications (below 5 MHz) a relatively higher weight ratio may be selected for the particles 20-25% and about 25-30% for the polyolefin elastomer since the lens attenuation may be kept 2 dB/mm. In a higher frequency range (in between 5 MHz and 10 MHz), in order to keep the attenuation below 2 dB/mm, the lower weight ratio of the polyolefin elastomer in the blend may be selected, for example about 15%-20%.

Further, in step 36 the layer overlaying the CMUT cell is cured at a temperature sufficient to evaporate the remaining solvent (about 100° C., in the case of heptane) from the liquid mixture layer.

This method can be advantageously applied on industrial scale owing to the simplicity of the steps and large tolerance of the ultrasound array's performance to the acoustic layer thickness. Each layer thickness can be increased by repeating the steps of dipping 34 and drying 36. Due to the possibility of the impedance optimization in steps 33 and 35 low attenuation properties of the hydrocarbon materials, a local thickness deviation in the acoustic window layer from the average value can be higher than the accepted standard in commonly used spray or spin coat manufacturing. In addition to this manufacturing method provides flexibility in different chip designs and electrical contact bonding implemented in the array.

The method can be also beneficially used for different chip size, especially in the area miniaturized ultrasound arrays, such as interventional devices and catheters.

FIG. 12 illustrates the principle design of an ultrasonic imaging system 202.

The ultrasound imaging system is generally denoted with reference numeral 202. The ultrasound imaging system 202 is used for scanning an area or volume of the body, e.g. of a patient 201. It is to be understood that the ultrasound system 202 may also be used for scanning other areas or volumes, e.g. body parts of animals or other living beings.

For scanning the patient 201, an ultrasound probe 200 may be provided. In the embodiment shown, the ultrasound probe 200 is connected to a console device 203. The console device 203 is shown in FIG. 12 as a mobile console. This console 203 may, however, also be realized as a stationary device. The console device 203 is connected to the probe 200 via an interface 206 formed in a wired manner. Further, it is contemplated that the console device 203 may also be connected to the probe 200 in a wireless manner, for example using UWB transmission technology. The console device 203 may further comprise an input device 205. The input device may have buttons, a key pad and/or a touchscreen to provide an input mechanism to a user of the ultrasound imaging system 202. Additionally or alternatively, other mechanisms may be present in the input device 205 to enable a user to control the ultrasound imaging system 202.

Further, the console device 203 comprises a display 204 to display data generated by the ultrasound imaging system 202 to the user. By this, the volume within the patient 201 that is scanned via the ultrasound probe 200 can be viewed on the console device 203 by the user of the ultrasound system 200.

The ultrasound probe 200 comprises the CMUT transducer array constructed in accordance with the present invention.

The invention claimed is:

1. An ultrasound probe comprising:
   a capacitive micro-machined ultrasound transducer (CMUT) cell comprising:
      a substrate;
      a first electrode;
      a cell membrane comprising a second electrode, wherein the cell membrane opposes the first electrode and the substrate with a cavity therebetween, wherein the membrane is arranged to vibrate upon a cell activation;
   an acoustic lens overlaying the CMUT cell, wherein the acoustic lens comprises:
      a first layer comprising a thermoset elastomer selected from a hydrocarbon family such that the thermoset elastomer is formed of only hydrogen and carbon atoms, wherein the first layer has an inner surface arranged to face the array and an outer convex shaped surface arranged to oppose the inner surface; and
      a second layer coupled to the outer surface of the first layer and comprising thermoplastic polymer polymethylpentene and an elastomer selected from a polyolefin family (POE) blended therein,
   wherein the first layer has a first acoustic wave velocity and the second layer has a second acoustic wave velocity, said second wave velocity is larger than the first wave velocity, wherein the first layer is in direct contact with the cell membrane,
   wherein the thermoset elastomer comprises polybutadiene,
   wherein the first layer including polybutadiene further comprises particles embedded therein for acoustic impedance adjustment of the first layer, and
   wherein the particles in the first layer include ceramic particles and the selected elastomer comprises a copolymer having a first monomer being an alpha olefin and a second monomer being ethylene.

2. The ultrasound probe according to claim 1, wherein the selected elastomer is a thermoplastic elastomer (TPE).

3. The ultrasound probe according to claim 1, wherein a percentage by weight of the particles based on a total weight of the first layer relates to a percentage by weight of the elastomer based on a total weight of the second layer, such that acoustic impedance of the first layer is substantially the same as the acoustic impedance of the second layer.

4. The ultrasound probe according to claim 3, wherein the acoustic impedance of the first and the second layers is around 1.6 MRayl.

5. The ultrasound probe according to claim 1, wherein the first monomer comprises octane.

6. The ultrasound probe according to claim 5, wherein the ceramic particles include zirconium dioxide ($ZrO_2$) particles.

7. The ultrasound probe according to claim 6, wherein a percentage by weight of the ceramic particles based on the total weight of the first layer is at most 25% and the percentage by weight of the elastomer based on the total weight of the second layer is at most 40%.

8. The ultrasound probe according to claim 6, wherein the percentage by weight of the particles based on the total weight of the first layer is 25% and the percentage by weight of the elastomer based on the total weight of the second layer is 20%.

9. The ultrasound probe according to claim 1, wherein an acoustic impedance difference between the first layer and the second layer is smaller than 0.3 MRayl.

10. The ultrasound probe according to claim 1, wherein the first acoustic wave velocity (v1) is 1470 m/s and the second acoustic wave velocity (v2) is 1900 m/s.

* * * * *